United States Patent [19]

Lang et al.

[11] Patent Number: 5,084,579

[45] Date of Patent: Jan. 28, 1992

[54] BENZOFURAN COMPOUNDS

[75] Inventors: Gérard Lang, Saint Gratien; Serge Forestier, Claye-Souilly; Alain Lagrange, Chatou; Jean Maignan, Tremblay-les-Gonesse; Gérard Malle, Villiers sur Morin, all of France

[73] Assignee: L'Oreal, Paris, France

[21] Appl. No.: 670,190

[22] Filed: Mar. 14, 1991

Related U.S. Application Data

[63] Continuation of Ser. No. 407,155, Sep. 14, 1989.

[30] Foreign Application Priority Data

Sep. 19, 1988 [FR] France ................. 88 12173

[51] Int. Cl.$^5$ ............................................. C07D 307/93
[52] U.S. Cl. ........................................ 549/57; 549/457
[58] Field of Search ................ 549/57, 60, 457, 459, 549/460

[56] References Cited

PUBLICATIONS

Forestier et al., Document No. 2187455A, Sep. 9, 1987.

*Primary Examiner*—C. Warren Ivy
*Assistant Examiner*—Raymond Covington
*Attorney, Agent, or Firm*—Cushman, Darby & Cushman

[57] ABSTRACT

A benzofuran compound of the formula

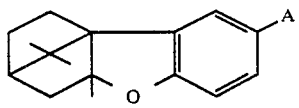

wherein A represents

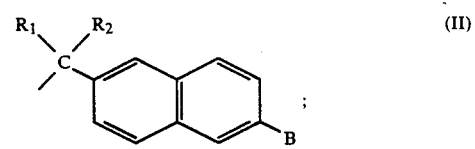

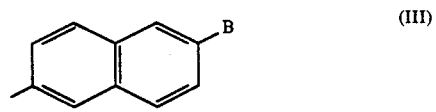

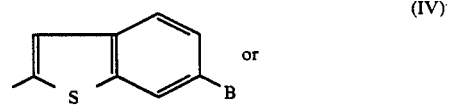

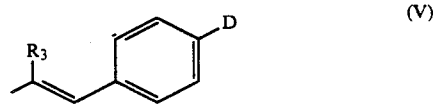

wherein $R_1$, $R_2$, $R_3$, B and D have various meanings. The benzofuran compound is usefully employed in pharmaceutical and cosmetic compositions.

4 Claims, No Drawings

BENZOFURAN COMPOUNDS

The invention relates to, as a new product, benzofuran derivatives, as well as to processes for their preparation. The invention also relates to the use of these new benzofuran compounds in cosmetic compositions and pharmaceutical compositions. They are useful either in human medicine or in veterinary medicine. These benzofuran compounds have a retinoid type activity, i.e. an activity analogous to that of vitamin A.

The therapeutic activity of vitamin A, in its acid, aldehyde or alcohol form, is quite well known in the field of dermatology (see, in this regard, "Experientia", Vol. 34, pages 1105–1119, 1978). This activity in the treatment of cutaneous proliferations, of acne, of psoriasis and of analogous disorders, is designated hereinafter by the generic expression "retinoid type activity". It has been noted that certain products having a structure analogous to vitamin A also exhibit a retinoid type activity. Moreover, certain ones of these compounds exhibit this activity in a manner clearly higher than vitamin A without the secondary effect of toxic hypervitaminose being proportionally increased (see in this regard "EUR. J. Med. Chem Chemica/Therapeutica, Jan.-Feb., 1980, 15 No. 1, pages 9–15).

In French application 2.596,050 of Feb. 13, 1987 there has been described benzofuran derivatives, having a 2,3,4,4a-tetrahydro-4a,10,10-trimethyl-1H-3,9b methano-dibenzofuran ring, abbreviated as TTMDBF, and having the formula

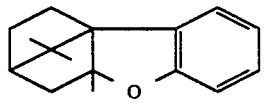

In this patent benzofuran compounds are described, which have a retinoid type activity, whose general formula is:

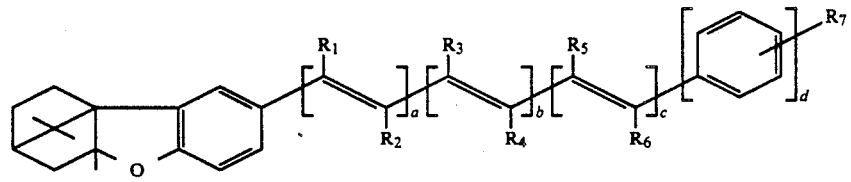

wherein a, b, c and d are whole numbers which can independently be 0 or 1, with the proviso that the sum a+b+c+d is greater than or equal to 2;

$R_1$, $R_2$, $R_3$, $R_4$, $R_5$ and $R_6$ represent, independently, hydrogen and $C_1$–$C_6$ alkyl;

$R_7$ represents a radical having the formula —$CH_2OR_8$ wherein $R_8$ represents hydrogen, $C_1$–$C_6$ alkyl, mono- or polyhydroxyalkyl having 2–6 carbon atoms,

wherein $R_9$ represents hydrogen; $C_1$–$C_6$ alkyl;

wherein R' and R", each independently, represents hydrogen, $C_1$–$C_6$ alkyl, mono- or polyhydroxyalkyl having 2–6 carbon atoms, $C_3$–$C_6$ alkenyl, or R' and R" together with the nitrogen atom to which they are attached form a heterocycle, the radical

also being able to be the residue of an amino acid or an aminated sugar; —$OR_{10}$ wherein $R_{10}$ represents hydrogen, $C_1$–$C_{20}$ alkyl, mono- or polyhydroxyalkyl having $C_2$–$C_6$ carbon atoms, or —$OR_{10}$ can be derived from a sugar; as well as the salts and isomers of this chemical compound.

The present invention relates to new benzofuran derivatives having a retinoid type activity. These new benzofuran derivatives can be employed in pharmaceutical preparations for the treatment of dermatologic disorders linked to a keratinization disorder (differentiation-proliferation), for the treatment of dermatologic disorders, or others, having an inflammatory and/or immuno-allergic component, for the treatment of atophy be it cutaneous or respiratory, for the treatment of illnesses of conjunctive tissue degeneration and of tumors, for the treatment of psoriasic rheumatism, or for the treatment of maladies in the ophthalmologic field, principally for the treatment of corneopathies.

The benzofuran compounds of the present invention can also be employed in cosmetic composition for body and hair hygiene.

The present invention concerns benzofuran compounds having the general formula (I):

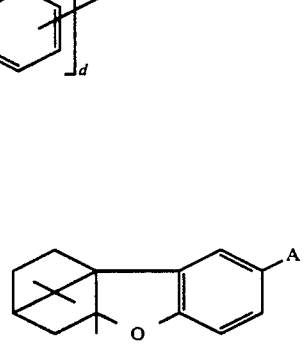

wherein
A represents group (II):

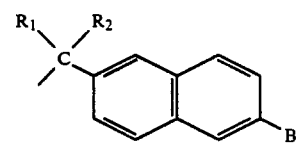

or group (III):

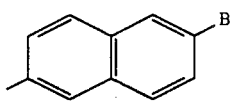

(III)

or group (IV):

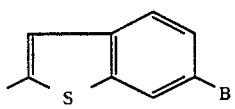

(IV)

or group (V):

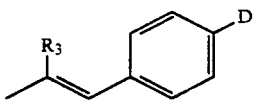

(V)

In group (II), $R_1$ represent hydrogen, OH, $C_1$-$C_4$ alkoxy, $C_1$-$C_4$ acyloxy or $NH_2$; $R_2$ represents hydrogen or $C_1$-$C_4$ acyloxy; or $R_1$ and $R_2$ taken together form an oxo, methano or hydroxyimino radical.

In groups (II) to (IV), B represents (a) CN; (b) oxazolinyl; (c) —$CH_2OR_4$ wherein $R_4$ represents hydrogen, $C_1$-$C_6$ alkyl, mono- or polyhydroxyalkyl having 2-6 carbon atoms, cyclopentyl, cyclohexyl or tetrahydropyranyl; (d)

wherein $R_5$ represents hydrogen; $C_1$-$C_6$ alkyl;

wherein $R_6$ and $R_7$ represent hydrogen, $C_1$-$C_6$ alkyl, $C_3$-$C_6$ alkenyl, cyclopentyl or cyclohexyl or even aralkyl or aryl optionally substituted, or $R_6$ and $R_7$ together aralkyl or aryl optional with the nitrogen atom to which they are attached form a ring or the radical

can be the residue of an amino acid or an aminated sugar; —$OR_8$ wherein $R_8$ represents hydrogen, $C_1$-$C_{20}$ alkyl, mono- or polyhydroxy alkyl having 2-6 carbon atoms, —$OR_8$ also being able to be a derivative of a sugar; (e) a radical D representing either an —SH residue or an —$S(O)n$ $R_9$ residue wherein n ranges from 0 to 2 inclusive, $R_9$ represents (i) $C_1$-$C_6$ alkyl substituted or not by one or more $C_2$-$C_6$ alkoxycarbonyl groups, one or more carboxyl groups, one or more amino or dialkylamino groups or being able to be an amino acid residue; (ii) $C_3$-$C_6$ alkenyl; (iii) mono- or polyhydroxyalkyl having 2-6 carbon atoms; (iv) and when n is equal to 1 or 2, hydroxy, $C_1$-$C_6$

wherein $R_6$ and $R_7$ have the meanings given above.

In group (V), D has the meaning given above and $R_3$ represents $C_1$-$C_6$ alkyl.

The invention also relates to the salts and isomers of the above compounds.

The present invention concerns, more particularly, compounds of formula (I) wherein A is group (II) wherein B is either $COR_5$ wherein $R_5$ is

wherein $R_6$ is hydrogen and $R_7$ is $C_1$-$C_6$ alkyl, or $COOR_8$ wherein $R_8$ is hydrogen or $C_1$-$C_{20}$ alkyl.

The present invention also relates, more particularly, to compounds of formula (I) wherein A is group (III) wherein B is either $COR_5$ wherein $R_5$ is

wherein $R_6$ is hydrogen and $R_7$ is $C_1$-$C_6$ alkyl, or —$COOR_8$ wherein $R_8$ is hydrogen or a $C_1$-$C_{20}$ alkyl.

The compounds of formula (I) where A is group (IV) are, preferably, those where B is $COOR_8$ wherein $R_8$ is hydrogen or a $C_1$-$C_{20}$ alkyl.

The compounds of formula (I) where A is group (V) are, preferably, those where D is —S—$CH_3$.

The present invention also relates to processes for the preparation of the benzofuran compounds defined above.

The compounds of formula (I) in which A is group (II) are prepared in the following manner: There is first prepared, most often, the compound in which $R_1$ and $R_2$ together form an oxo radical and B represents $CO_2R_8$ wherein $R_8$ is a $C_1$-$C_{20}$ alkyl. This product then serves as the initial reactant for the production of other compounds.

This initial reactant is prepared in the following manner: in a first stage, the product (1), i.e. 6-alkoxycarbonyl-2-naphthalene carboxylic acid is tranformed into the corresponding chloride by the action of thionyl chloride, in accordance with the following reaction scheme:

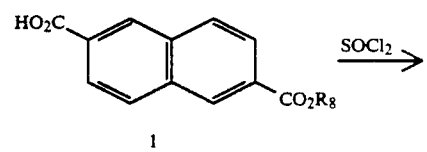

1

-continued

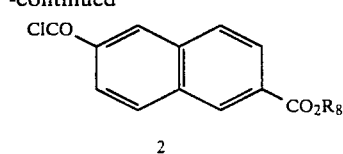

The magnesium derivative (4) can be prepared in anhydrous tetrhydrofuran (THF) at reflux and the condensation of the acid chloride (2) is carried out at a temperature of 0° C. in the same solvent.

There can, for example, then be prepared an amide (7) starting with the ketoacid (6) in accordance with the following reaction scheme:

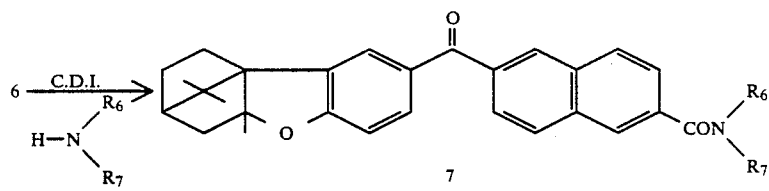

In the second stage, the resulting acid chloride (2) is reacted with 2,3,4,4a-tetrahydro-4a, 10,10-trimethyl-1H-3,9b methano-dibenzofuran (3) either directly by a Friedel Crafts reaction, or by reaction with a previously prepared halogenated magnesium derivative (4), in accordance with the following reaction scheme:

by the action of an amine having the formula

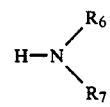

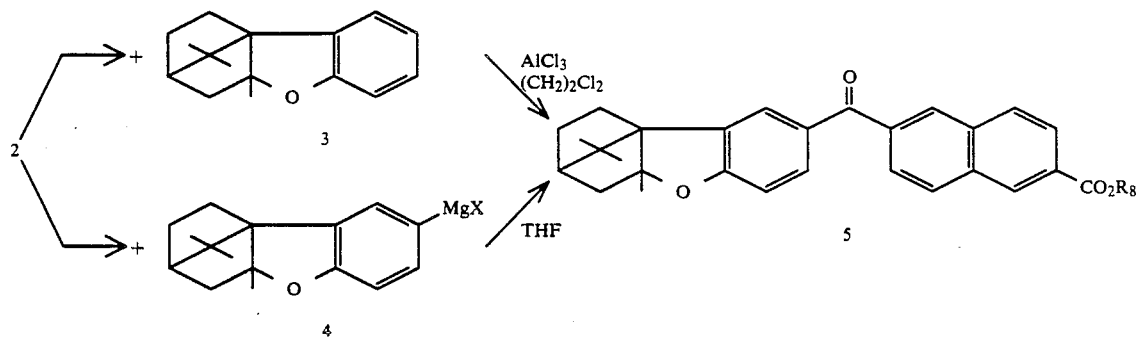

wherein X represents Br or Cl, the resulting benzofuran ester (5) then being saponified to give the ketoacid (6) in accordance with the following reaction scheme:

in the presence of N,N'-carbonyldiimidazole (CDI).

For certain meanings of $R_8$, in particular when $R_8$ represents a monohydroxy- or polyhydroxy alkyl, it is

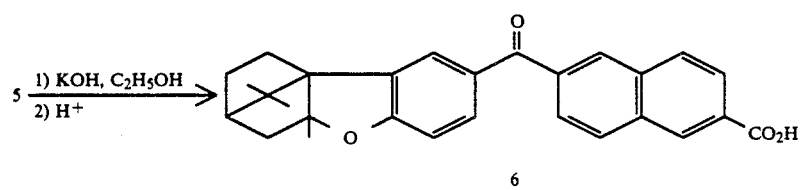

The benzofuran ester (5) or the benzofuran acid (6) serves then, in a known manner, as starting products for the production of other derivatives of formula (I) wherein A is group (II).

The product (1), i.e. 6-alkoxycarbonyl-2-naphthalene carboxylic acid can, for example, be obtained by the monosaponification reaction of a 2,6-dialkyl naphthalene dicarboxylate, starting preferable with 2,6-dimethyl naphthalene dicarboxylate which is a commercial product.

preferable to prepare the ketoacid (6) starting with the methyl ester (5) in which $R_8$ is $CH_3$ and then esterifying the acid thus obtained into the ester of the selected alcohol according to known methods.

The compound of formula (I) in which A represents group (II), $R_1$=H, $R_2$=OH and B=$CH_2OH$ is obtained by the reduction of the ketoacid (6) in the presence of lithium aluminum hydride in tetrahydrofuran (THF) in accordance with the following reaction scheme:

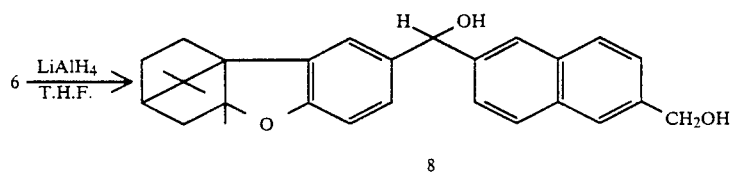

The resulting diol (8) can then be oxidized in the presence of pyridinium chlorochromate (PCC) which leads to the ketoaldehyde (9) in accordance with the following reaction scheme:

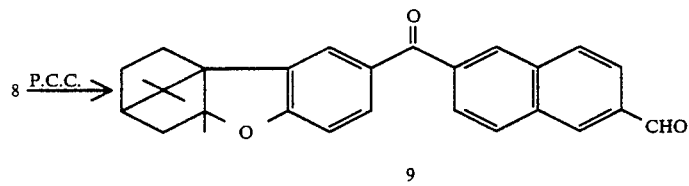

The compounds of formula (I) in which A represents group (II), R₁=H, R₂=OH and B=CO₂R₈ are obtained starting with the ketonic derivatives by reduction with sodium borohydride in tetrahydrofuran.

The compounds of formula (I) in which A represents group (II) and R₁ and R₂ are hydrogen, are obtained by reduction with zinc of the corresponding ketonic derivatives in acetic acid, in the presence of HCl. These reduction reactions of the carbonyl must, however, be compatible with the nature of the radical B. The reduction of the carbonyl raises no difficulty when B=CO₂H, but it can be desirable optionally for other B radicals to insure their protection.

The acyloxy compounds of formula (I) in which A represents group (II), with R₂=H and R₁=C₁-C₄ acyloxy, are obtained by reacting an anhydride or acid chloride with a compound of formula (I) in which A represents group (II) and R₂=H and R₁=OH.

The acyloxy compounds of formula (I) in which A represents group (II), with R₁=H and R₂=C₁-C₄ alkoxy, are obtained in the same way starting with corresponding compounds for which R₁=H and R₂=OH, in accordance with known etherification procedures.

For the preparation of the acyloxy and alkoxy derivatives, it is preferable that the radical B is an ester or acid function.

The compounds of formula (I) in which A represents group (III) are obtained by a coupling reaction between a halogenated benzofuran compound of formula (10) and a halogenated derivative of naphthalene of formula (11):

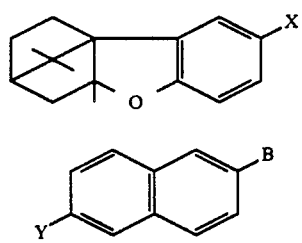

in which B has the same meaning as that given above and X and Y represent a halogen atom, the halogenated benzofuran compounds of formula (10) being trans- formed into its magnesium, lithium or zinc derivative and then coupled with the halogenated derivative of naphthalene of formula (11) by using, as reaction catalyst, a transition metal or one of its complexes. Representative catalysts include, in particular, derivatives of nickel, and palladium and, in particular, compounds of Ni$_{II}$, for example NiCl₂, with various phosphines. The coupling reaction is generally carried out at a temperature between −20° C. and +30° C. in an anhydrous solvent, such as for example dimethylformamide or tetrahydrofuran. The resulting product can be purified by recrystallization or by chromatography on a silica column. It goes without saying that the choice of the halogenated derivative of naphthalene of formula (11), for the coupling reaction with the halogenated compound of formula (10), must be such that it can lead by subsequent reaction to the various meanings of the radical B defined above.

The compounds of formula (I) in which A is group (IV) are prepared by condensing a benzofuran derivative of carboxylic acid (12) with a thiol (13), in accordance with the following reaction scheme:

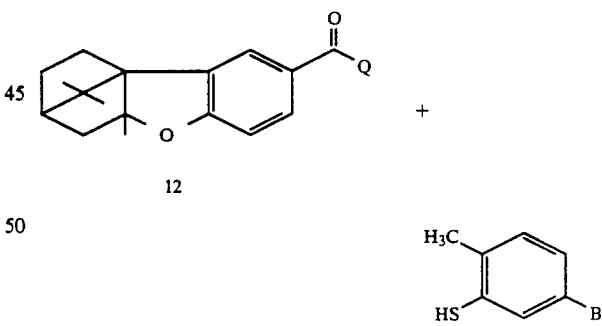

wherein Q is OH or Cl.

An intermediate product (14) is obtained, this intermediate product having the formula:

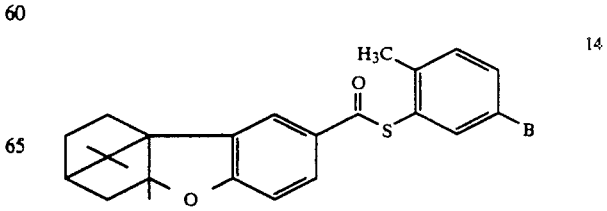

It is then submitted to bromination so as to obtain a bromomethylated derivative (15) of the formula:

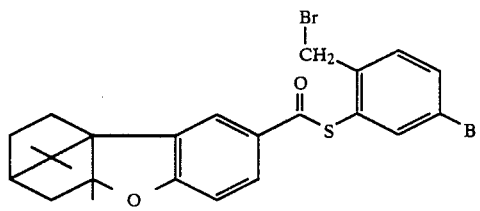

The product (15) is then submitted to a reaction with a triarylphosphine and then to a cyclization reaction to produce product (16) having the formula:

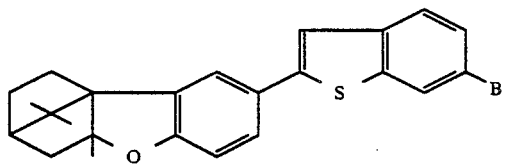

The bromination reaction is carried out, preferably, by means of N-bromosuccinimide in benzene or dry carbon tetrachloride at a temperature between 70° C. and 90° C. in the presence of a radical initiator such as benzoyl peroxide, optionally under luminous irradiation.

The cyclization reaction is, preferably, carried out in the presence of a base such as an alkali metal hydroxide or an alkali metal carbonate, for example, lithium hydroxide or potassium carbonate, an alkali metal hydride, for example, sodium hydride, an alkali metal alcoholate, for example, sodium methylate or potassium tert. butylate, a tertiary amine, for example, triethylamine, diisopropylethyl amine or diazabicycloundecene, an alkali metal amide, for example sodium amide or lithium diisopropylamide. The reaction temperature ranges between −10° C. and +150° C. There is employed, preferably, a dipolar aprotic solvent (dimethyl sulfoxide or dimethylformamide), an alcohol or an ether (dioxane or tetrahydrofuran).

The compounds of formula (I) in which A represents group (IV) are prepared in accordance with one of the following three processes:

(1) First process

A benzofuran compound having the formula:

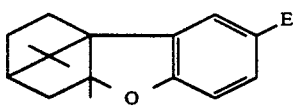

is reacted with a compound having the formula:

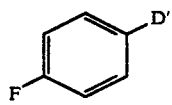

in which D' represents —SO$_3$⊕M⊖, —SO$_2$⊕M⊖, alkylthio, alkylsufinyl or alkylsulfonyl, wherein the alkyl moiety has 1-6 carbon atoms E represnets R$_3$—CH—P[Z]$_3$⊕Y⊖ when F represents formyl or indeed represents

when F represents

Z being aryl, T being C$_1$-C$_6$ alkoxy, Y⊖ being an anion of a mineral or organic acid and M⊕ being a cation of an alkali or alkaline earth metal and R$_3$ having the meaning given above.

(2) Second process

A strong base is reacted with a compound of the formula:

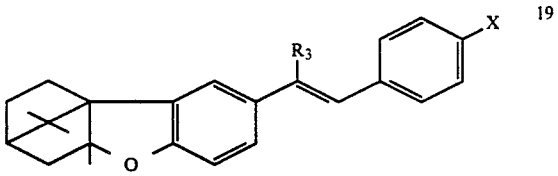

wherein R$_3$ has the meaning given above and X represents a halogen atom. The resulting product is then submitted to the action of SO$_2$.

(3) Third process

A compound having the formula:

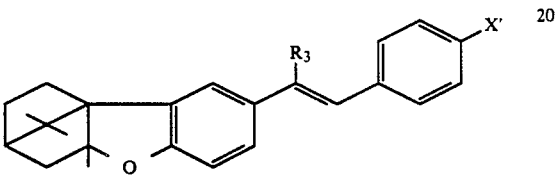

in which R$_3$ has the meaning given above and X' represents an alkylthiocarbamoyl residue wherein the alkyl moiety has 1-6 carbon atoms is reacted with a base or metal hydride.

The first process can be employed in accordance with the classic conditions of a Wittig reaction or Horner reaction.

In the second process, the strong base employed is, preferably, butyllithium. The reaction is carried out in an inert solvent such as an ether or a hydrocarbon at a temperature near 0° C.

The base employed in the third process is an alkali metal hydroxide such as potassium hydroxide. The reaction is effected in an inert solvent at a temperature ranging from ambient temperature to the boiling point of the solvent. In accordance with this third process, a compound of formula (I) in which A represents group (IV) with D=SH is obtained.

In the compounds of general formula (I) where A is group (II), (III) or (IC), the functional modifications of the B residue or D residue can be obtained in accordance with known methods carboxylic acid→ester ester→carboxylic acid acid→acid chloride acid chloride→amide acid→amide acid→alcohol alcohol→aldehyde amide→amine thiol→thioether thioether→sulfoxide tioether→sulfone sulfonic acid→sulfonic ester sulfonic acid→sulfonamide sulfinic acid→sulfinic ester Michael addition of thiols Also, the transformation of carboxylic, sulfonic or sulfinic acids into corresponding salts or salts into corresponding acids can be achieved in accordance with known methods.

The compounds of formula (I) are used for the treatment of dermatologic disorders linked to a keratinization disorder based on differentiation and proliferation, principally for the treatment of acne vulgaris, comedons, polymorphs, nodulo cystic acne, conglobata, senile acne, secondary acne such as solar acne, medicinal acne and professional acne. The compounds are also indicated for other types of keratinization disorders, principally, ichthyoses, ichthyosiform states, Darier malady, palmoplnataire kerotodermie, leucoplasie and leucoplasiform states and lichen.

The compounds of the present invention are also employed to treat other dermatologic ailments linked to a keratinization disorder with an inflammatory and/or immunoallergic component and, principally, all forms of psoriasis, be it cutaneous, mucous or ungual and even psoriasic rheumatism; they can also be employed in the treatment of cutaneous atophy such as eczema or respiratory atophy.

These compounds can also be used to treat all dermal or epidermal proliferations, that are benign or malignant, that are of viral origin such as common warts, surface warts and verruciform epidermodysplasie; the proliferations can also be induced by ultra-violet rays such as baso epithelioma and cellular spino.

These compounds can also be employed to treat other dermatologic disorders such as vesicular maladies and collagen maladies.

Finally, these compounds also are useful in the field of ophthalmology for the treatment of corneopathies.

The present invention also then relates to a new medicinal composition intended principally for the treatment of the above mentioned disorders, comprising, in a pharmaceutically acceptable support, as the active substance, an effective amount of at least one compound of formula (I) and/or at least one of its isomers and/or at least one of its salts.

When the compounds of formula (I) are employed topically, good activity is observed on a very large range of dilution; there can be used, principally, concentrations of the active substance, ranging from 0.0005% to 2% by weight based on the total weight of the composition. It is, however, possible to employ higher concentrations when it is considered necessary for a particular therapeutic application; however, the preferred concentration of the active substance ranges from 0.002 to 1 percent by weight.

The topical compositions are advantageously provided in the form of ointments, gels, creams, salves, powders, tinctures, solutions, suspensions, emulsions, lotions, sprays, stamps, or impregnated pads. The compounds of formula (I) are blended with non-toxic inert supports, generally a liquid or paste, appropriate for topical treatment.

The aforementioned pharmaceutically active substances can also be employed enterally. When taken orally, the said active substances are administered at a rate of about 2 $\mu$g up to 2 mg per day and per kilogram of body weight; an excessive posology can manifest itself in the form of hypervitaminose A, recognizable with its symptoms, and can cause fear of a hepatic toxicity, requiring biologic control of the hepatic function. The dose required can be administered in one or several dosages. For oral administration, the appropriate forms are, for example, tablets, gelules, lozenges, syrups, suspensions, emulsions, solutions, powders, and granules; a preferred method of administration comprises using gelules containing 0.1 mg to about 1 mg of the active substance.

The pharmaceutically active substance of the present invention can be administered parenterally, in the form of solutions or suspensions for perfusions or intravenous or intramuscular injection. In this case, the said active substance is administered at a rate of about 2 $\mu$g up to 2 mg per day and per kilogram of body weight; a preferred method of administration comprises using solutions or suspensions containing from 0.01 mg to about 1 mg of substance per ml.

When the pharmaceutically active substances of formula (I) are employed ocularly, they are provided, advantageously, in the form of solutions or dilutable powders for eyewashes.

The pharmaceutically acceptable support can comprise water, gelatin, lactose, starch, talc, petrolatum, gum arabic, polyalkylene glycols, or magnesium stearate. The tablets, powders, lozenges, granules or gelules can contain binders, fillers or pulverulent supports. The solutions, creams, suspension, emulsions or syrups can contain diluents, solvents or thickening agents.

The compounds of formula (I), as well as their salts and isomers, can also be employed in the cosmetic field, in particular in body and hair hygiene and, principally, in the treatment of skin having acne tendencies, physiologically dry skin, seborrhea, combatting falling hair, promotion of hair growth, combatting the oily appearance of the hair and skin and combatting ageing of the skin. They also have a preventative power against the harmful effects of the sun.

The compounds, in accordance with the invention, exhibit excellent comedolytic activity in the rhinomouse test described by Bunne et al in the International Journal of Cosmetic Science, 3, 23-28 (1981).

The present invention also then relates to a new cosmetic composition comprising, in a cosmetically acceptable support, as an active substance, at least one compound of formula (I) and/or at least one of its isomers and/or at least one of its salts; this composition can be provided in the form of a lotion, gel, cream, foam, soap, shampoo or analogous forms.

The concentration of the cosmetically active substance ranges from 0.0005 to 2 weight percent and, preferably from 0.01 to 1 weight percent, relative to the total weight of the composition.

In the treatment of the above mentioned disorders, the compounds according to the invention, employed in the above defined compositions, act by increasing follicular epithelial production of non-adherent cells, dislodging as well as expelling the content of acne comedons. These compound reduce the size of the sebaceous glands and partially inhibit the secretion of sebum.

The compositions according to the invention can contain inert additives, or even pharmacodynamically or cosmetically active substances and, principally, hydrating agents, such as thiamorpholinone and its derivatives or urea; anti-seborrhea agents such as S-carboxylmethyl cysteine or S-benzyl cysteamine, theirs salts and their derivatives and tioxolone; anti-acne agents such as benzoyl peroxide; antibiotics such as erythromycin and its esters, neomycin, tetracyclines or 4,5-polymethylene-3-isothiazolones; agents favoring hair growth sold under the trade name "Mixoxidil" and its derivatives, anthralin and its derivatives, 7-chloro-3-methyl-1,2,4-benzothiadiazine-1,1-dioxide sold under the trade name "Diazoxide", 5,5-diphenyl-2,4-imidazolidinedione sold under the trade name "Phenitoin", oxapropanium iodide or retinoic acid and its retinoid derivatives; steroidal or non-steroidal anti-inflammatory agents; carotenoids and, principally, $\beta$-carotene; anti-psoriasic agents such as anthralin and its derivatives, 5,8,11,14-eicosatetraynoic acid and 5,8,11-eicosatriynoic acid, their salts and their amides.

The compositions according to the present invention can also contain flavor improving agents, preservatives, stabilizers, humidity regulating agents, pH regulating agents, emulsifiers, UV-B and UV-A filters, antioxidants such as α-tocopherol, butylhydroxyanisole or butylhydroxytoluene.

To better understand the invention several non-limiting examples of the benzofuran compounds, processes for preparing them and compositions containing them are given below.

EXAMPLE 1

Preparation of the compound of formula (I) below, wherein A is group (IV) and B is $CO_2R_8$ wherein $R_8=CH_3$:

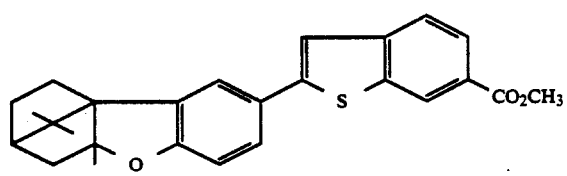

This preparation involves five steps, (a)-(e).

(a) preparation of starting compound: 2,3,4,4a-tetrahydro-4a,10,10-trimethyl-1H-3,9b methanodibenzofuran (TTMDBF) having the formula:

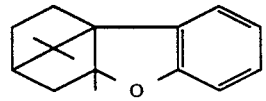

This product is obtained in accordance with the operating procedures described by J.L. Fry and W.J. West, J. Org. Chem. 1981, v. 46 (10) 2177-2179.

(b) preparation of the ketonic derivative of the below formula starting with TTMDBF

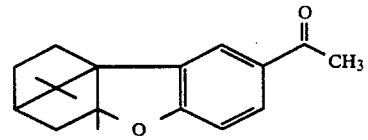

There is slowly added a solution of 9.2 g of TTMDBF and 3.2 cm$^3$ of acetyl chloride in 60 cm$^3$ of dichloromethane to a solution, previously cooled to $-10°$ C., of 6 g of aluminum chloride in 60 cm$^3$ of dichloromethane. The reaction mixture is stirred for two hours, while letting its temperature return to ambient temperature. The reaction mixture is poured into a saturated solution of ammonium chloride and the organic phase is extracted with ether. The organic phases are combined, dried on sodium sulfate and the solvent is distilled under reduced pressure. The resulting residue is recrystallized in ethanol. Melting point$=130°$ C. UV spectrum (chloroform): $\lambda max=291$ nm, $\epsilon=14230$ Analysis of the product obtained gives the following results:

| Analysis | Calculated for $C_{18}H_{22}O_2$ | Found |
|---|---|---|
| C | 79.96 | 80.01 |
| H | 8.20 | 8.20 |
| O | 11.84 | 11.68 |

(c) preparation of the acid corresponding to the ketonic derivative prepared in step (b), having the formula:

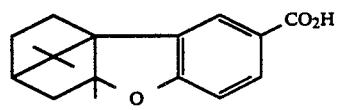

While maintaining the temperature at 0° C., 18 cm$^3$ of bromine are added to a solution of 42 g of soda in 210 cm$^3$ of water. After 15 minutes, there are added 16.5 g of the ketonic derivative, obtained in step (b), in solution in 100 cm$^3$ of dioxane. The mixture is stirred for 15 minutes at 0° C. while letting the temperature return to ambient temperature. The reaction mixture is heated for 2 hours at 50° C. After cooling, 18.1 g of sodium metabisulfite in solution in 140 cm$^3$ of water are added and then, slowly, 84 cm$^3$ of concentrated HCl. The reaction mixture is extracted with ether and after distillation of the solvent under reduced pressure, recrystallized in ethyl acetate. 12 g of the expected product in the form of white crystals, having the following characteristics: Melting point$=>260°$ C.; UV spectrum (CHCl$_3$): $\lambda max=270$ nm, $\epsilon=12000$, are obtained.

Analysis of the product obtained gives the following results:

| Analysis | Calculated for $C_{17}H_{20}O_3$ | Found |
|---|---|---|
| C | 74.97 | 74.90 |
| H | 7.40 | 7.43 |
| O | 17.62 | 17.49 |

(d) preparation of the compound having the following formula:

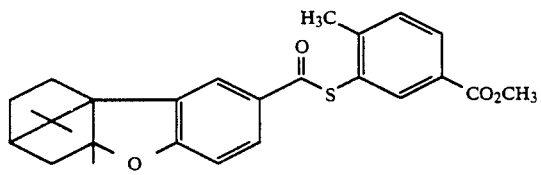

by reaction with the acid obtained in step (c) with a thiol.

There is heated for 3 hours at 70° C. a mixture of 5 g of the compound obtained in step (c), 1.2 cm³ of phosphorus trichloride and 50 cm³ of toluene. The reaction mixture is filtered on diatom earth sold under the name "Celite" by Manville Products Corporation and the solvent is distilled under reduced pressure. The residue is redissolved in 50 cm³ of tetrahydrofuran. 3.5 g of 5-methoxycarbonyl-2-methyl thiophenol and 3 cm³ of triethylamine in solution in 20 cm³ of triethylamine in solution in 20 cm³ of tetrahydrofuran are added.

After one hour of stirring, the reaction mixture is poured into water and the mixture is extracted with ethyl acetate. The organic phase is washed initially with a saturated solution of sodium bicarbonate and then with diluted soda and finally with water. After drying the organic phase, distilling the solvent under reduced pressure and recrystallizing in ethanol, 5.8 g of the expected product having the following characteristics: Melting point=145° C.; UV spectrum $(CHCl_3)-\lambda max=305$ nm, $\epsilon=22800$ are obtained.

Analysis of the product obtained gives the following results:

| Analysis | Calculated for $C_{26}H_{28}O_4S$ | Found |
|---|---|---|
| C | 71.53 | 71.41 |
| H | 6.46 | 6.32 |
| O | 14.66 | 14.57 |
| S | 7.34 | 7.25 |

(e) preparation of the compound of the below formula by bromination and cyclization of the product obtained in step (d)

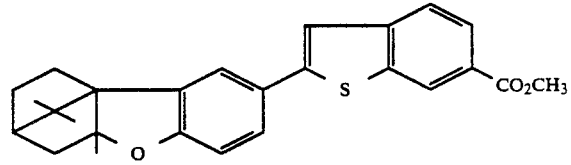

There is heated at reflux for 3 hours a mixture of 2.5 g of the compound obtained in step (d) and 1.13 g of N-bromosuccinimide in 100 cm³ of carbon tetrachloride under UV radiation. The mixture is cooled and the succinimide formed is filtered. The solvent is distilled under reduced pressure and the residue, dissolved in 50 cm³ of toluene, is rapidly filtered on silica gel. The organic phase is diluted with 50 cm³ of toluene. 1.5 g of triphenylphosphine are added and the mixture is stirred for 4 hours at 100° C. The solvent is distilled and the residue is treated with 100 cm³ of isopropylether. After filtration and evaporation of the solvent, the residue is suspended in 100 cm³ of tetrahydrofuran. 0.86 cm³ of diazabicycloundecene is slowly added and the mixture is stirred for 2 hours at ambient temperature. After evaporation of the solvent and recrystallization in ethanol, 0.6 g of the expected product having the following characteristics: Melting point=156° C.; UV spectrum $(CHCl_3)$: $\lambda max=342$ nm, $\epsilon=26100$ is obtained.

Analysis of the product obtained gives the following results:

| Analysis | Calculated for $C_{26}H_{26}O_3S$ | Found |
|---|---|---|
| C | 74.61 | 74.82 |
| H | 6.26 | 6.27 |
| O | 11.47 | 11.61 |
| S | 7.66 | 7.61 |

EXAMPLE 2

Preparation of the compound of formula (I) below where A is group (IV) and B is $COOR_8$ wherein $R_8=H$

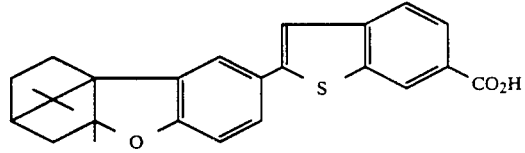

There is heated for 2 hours at 70° C. a mixture of 1.9 g of the compound obtained in step (e) of Example 1 and 2 g of potash in 200 cm³ of ethanol and 50 cm³ of water. After distillation of the ethanol and dilution with water, the mixture is acidified by the addition of 1N HCl. The reaction mixture is filtered, washed with water and the resulting precipitate is dried. After recrystallization in an ethanol/tetrahydrofuran mixture, 1.45 g of the expected product having the following characteristics: Melting point=>260° C.; UV spectrum (MeOH): $\lambda max=331$ nm, $\epsilon=27800$ ar obtained.

Analysis of the product obtained gives the fol owing results:

| Analysis | Calculated for $C_{25}H_{24}O_3S.0.5H_2O$ | Found |
|---|---|---|
| C | 72.55 | 72.81 |
| H | 6.05 | 6.04 |
| O | 13.54 | 13.03 |
| S | 7.74 | 7.57 |

EXAMPLE 3

Preparation of the compound of formula (I) below where A is group (III) and B is COOR$_8$ wherein R$_8$=H

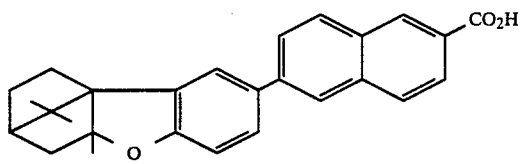

(a) preparation starting with TTMDBF of the brominated compound having the formula:

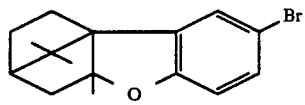

22.8 g of TTMDBF, obtained in step (a) of Example 1 are suspended in 50 cm$^3$ of tetrahydrofuran. At 15° C. a solution of 17.8 g of N-bromosuccinimide in 50 cm$^3$ of dimethylformamide is added over a 40 minute period. The temperature slowly rises from 15° to 30° C. A precipitate appears little by little. The reaction mixture is poured into 500 cm$^3$ of water. After extraction with 500 cm$^3$ of dichloromethane and distillation of the solvent under reduced pressure, 22 g of the expected product in the form of a white powder are obtained.

(b) preparation of the compound having the formula:

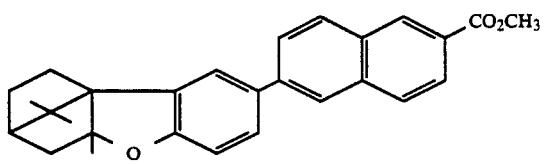

There is heated at reflux under nitrogen for 2 hours a mixture containing 18.4 g of the compound obtained in step (a), above, 2.2 g of magnesium and an iodine crystal in 200 cm$^3$ of anhydrous tetrahydrofuran. The mixture is cooled to 20° C. and 13.5 g of zinc bromide are added. The mixture is stirred for 1 hour at ambient temperature and then 5.4 g of methyl 6-bromonaphthalene carboxylate and 0.1 g of, as the catalyst, NiCl$_2$-1,2-(diphenylphosphino) ethane (DPPE) are added. The mixture is stirred for 1 hour at ambient temperature and then poured into a saturated solution of ammonium chloride. After extraction with ethyl acetate and distillation of the solvent, the residue is recrystallized in an acetonitrile/heptane mixture. 7 g of the expected product in the form of white crystals are obtained. Melting point=210° C.; UV spectrum (CH$_2$Cl$_2$): λmax=330 nm, ε=23700 are obtained.

Analysis of the product obtained gives the following results:

| Analysis | Calculated for C$_{28}$H$_{28}$O$_3$ | Found |
|---|---|---|
| C | 81.52 | 81.54 |
| H | 6.84 | 6.83 |
| O | 11.64 | 11.49 |

(c) preparation of the compound having the formula:

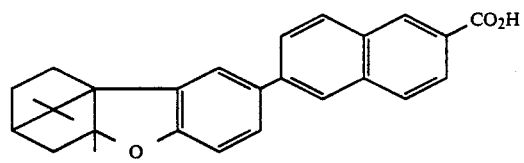

There is heated for 2 hours at 70° C., a mixture containing 6.5 g of the compound obtained in stage (b), above, of this Example, and 2 g of potash in 200 cm$^3$ of ethanol and 50 cm$^3$ of water. After distillation of the ethanol and dilution with water, the mixture is acidified by the addition of IN HCl. The reaction mixture is filtered, washed with water and the resulting precipitate is dried. After recrystallization in a mixture of ethanol and tetrahydrofuran 5 g of the expected product are obtained.

The product obtained has the following characteristics: Melting point=250° C.; UV spectrum (CH$_2$Cl$_2$): λmax=330 nm, ε=23500.

Analysis of the product obtained gives the following results:

| Analysis | Calculated for C$_{27}$H$_{26}$O$_3$ | Found |
|---|---|---|
| C | 81.38 | 81.60 |
| H | 6.57 | 6.60 |
| O | 12.05 | 12.29 |

EXAMPLE 4

Preparation of the compound of formula (I) below where A is group (III) and B has the formula CO-R$_5$ is

wherein R$_6$=H and R$_7$=C$_2$H$_5$

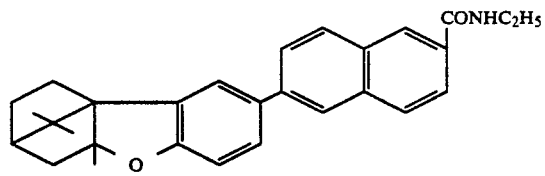

A suspension of 1 g (2.5 mmoles) of the acid obtained in Example 3, above, and 0.45 g of N,N'-carbonyldiimidazole in 40 cm$^3$ of dicholoromethane is stirred for 30 minutes. The solvent is distilled under reduced pressure. The reaction mixture is cooled to 0° C. and then 40 cm$^3$ of tetrhydrofuran and 1 cm$^3$ of anhydrous ethylamine are added. The mixture is stirred for 1 hour and then poured into water. The mixture is extracted with ethyl acetate. The organic phase is washed with water and then dried on sodium sulfate. After distillation of the solvent under reduced pressure, the residue is recrystallized in an ethanol-water mixture.

The product obtained has the following characteristics: Melting point = >260° C.; UV spectrum (CH$_2$Cl$_2$): λmax=330 nm, ε=24000.

Analysis of the product obtained gives the following results:

| Analysis | Calculated for C$_{29}$H$_{31}$NO$_2$.1/3 H$_2$O | Found |
|---|---|---|
| C | 80.74 | 80.64 |
| H | 7.35 | 7.36 |
| N | 3.25 | 3.27 |
| O | 8.66 | 8.38 |

EXAMPLE 5

Preparation of the compound of formula (I) below where A is group (V) wherein R$_3$=CH$_3$ and D=S-CH$_3$

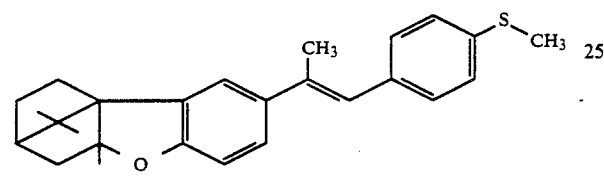

5.4 g of the product obtained in step (b) in Example 1 are suspended in 30 cm$^3$ of methanol and 2 cm$^3$ of water. 0.6 g of sodium borohydride is added and the mixture is stirred at ambient temperature for 16 hours. The reaction mixture is poured over ice. The precipitate and the organic phase are extracted three times using 60 cm$^3$ of ether. The organic phase is dried on sodium sulfate and the solvent is distilled under reduced pressure. 5.7 g of product are obtained which is then redissolved in 50 cm$^3$ of petroleum ether. The solution is cooled to about −10° C. and over a 30 minute period about 1.83 g of phosphorus tribromide are added while maintaining the temperature below −10° C. After the addition of the phosphorus tribromide, the mixture is stirred for 12 hours at ambient temperature. The reaction mixture is poured over ice and the mixture is extracted three times using 60 cm$^3$ of ether. The organic phase is washed with an aqueous solution of sodium bicarbonate and then with a saturated solution of sodium chloride. After drying on sodium sulfate and then evaporating the solvent, 5.5 g of yellow crystals are recovered which are redissolved in 50 cm$^3$ of toluene. 4.1 g of triphenylphosphine are added and the mixture is stirred initially for 12 hours at ambient temperature, then for 6 hours at 55° C. The reaction mixture is cooled and the resulting precipitate is filtered, washed with hexane and dried. 6.5 g of pale yellow product are obtained which is then redissolved in 100 cm$^3$ of methanol. 2 g of potassium carbonate and 1.1 g of 4-methylthio benzaldehyde are added and the mixture is heated at reflux for 4 hours. The reaction mixture is poured into water. After extraction with ethyl acetate and distillation of the solvent under reduced pressure, an oily residue is obtained which, after recrystallization in 95% ethanol, has the following characteristics: Melting point=130° C.; UV spectrum (CH$_2$Cl$_2$): λmax=309 nm, ε=30200.

Analysis of the product obtained gives the following results:

| Analysis | Calculated for C$_{26}$H$_{30}$OS | Found |
|---|---|---|
| C | 79.95 | 79.89 |
| H | 7.74 | 7.68 |
| O | 4.10 | 4.26 |
| S | 8.21 | 8.11 |

EXAMPLE 6

Preparation of the compound of formula (I) below where A is group (II), R$_1$ and R$_2$ form an oxo group, =O, and B=COR$_5$ wherein R$_5$ is —O—R$_8$ wherein R$_8$ is CH$_3$

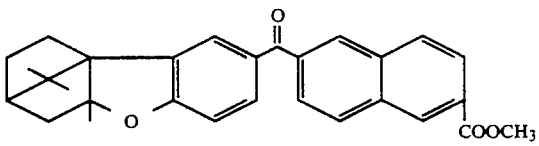

To a suspension of 2.39 g (10 mmoles) of TTMDBF, prepared in step (a) of Example 1, and 2.49 g (10 moles) of 6-methoxy carbontl-2-naphthalene carboxylic acid chloride in 50 cm$^3$ of anhydrous 1,2-dichloroethane, there are added, by portions over a 45 minute period, 2 g of anhydrous aluminum chloride. The mixture is stirred for 4 hours at ambient temperature and then poured into 20 cm$^3$ of ice water. The organic phase is decanted. The aqueous phase is again extracted with 50 cm$^3$ of dichloroethane. The dichloroethane phases are combined, washed with water, dried on sodium sulfate and concentrated under reduced pressure. The resulting crude oil is purified by chromatograph on silica gel 60 with elution initially by dichloromethane and then by ethyl acetate. The isolated white solid is recrystallized in a minimum of hexane. After drying, 2.9 g of 2-methyl-6-[(TTMDBF carbonyl] naphthalene carboxylate having the following characteristics: Melting point: 146°-148° C.; NMR $^1$H 80 MHz conforming to the expected structure, are obtained.

Analysis of the product obtained gives the following results:

| Analysis | Calculated for C$_{29}$H$_{28}$O$_4$ | Found |
|---|---|---|
| C | 79.06 | 78.96 |
| H | 6.41 | 6.43 |
| O | 14.53 | 14.37 |

EXAMPLE 7

Preparation of the compound of formula (I) below where A is group (II and R$_1$ and R$_2$ together form an oxo group, B is

wherein R$_5$ is Or$_8$ whrein R$_8$=H

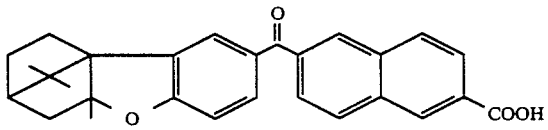

A suspension of 1.9 g (4.3 mmoles) of 2-methyl-6-[(TTMDBF) carbonyl] naphthalene carboxylate, obtained in accordance with Example 6, is stirred for 2 hours in a mixture of 25 cm³ of alcohol and 25 cm³ of 6N aqueous potash heated at reflux. After addition of 100 cm³ of water, the alcohol is removed by evaporation under a vacuum. The aqueous phase is diluted to about 300 cm³ and then acidified by the addition of 20 cm³ of 12N HCl. The resulting precipitate is filtered, washed thoroughly with water and dried on potash at 80°–100° C. After recrystallization in methanol, in the presence of animal charcoal and then a second recrystallization, also in methanol, 1.25 g of white crystals of 6-[(TTMDBF) carbonyl]-2-naphthalene carboxylic acid having the following characteristics: Melting point −271° C. NMR ¹H 250 MHz conforming to the structure, are obtained.

Analysis of the product obtained gives the following results:

| Analysis | Calculated for $C_{28}H_{26}O_4$ | Found |
| --- | --- | --- |
| C | 78.85 | 78.76 |
| H | 6.14 | 6.16 |
| O | 15.00 | 15.15 |

EXAMPLE 8

Preparation of the compound of formula (I) below wherein A is group (III), $R_1$ and $R_2$ together form an oxo group, B is $COR_5$ wherein $R_5$ is

wherein $R_6$ is H and $R_7$ is $CH_2CH_3$

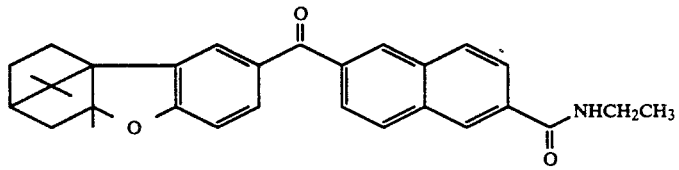

A suspension of 260 mg (0.6 mmoles) of 6[(TTMDBF) carbonyl]-2-naphthalene carboxylic acid, obtained in Example 7, and 120 mg (0.72 mmole) of N,N′-carbonyldiimidazole in 5 cm³ of anhydrous 1,2-dichloroethane is stirred for 1 hour at ambient temperature. The resulting solution is cooled to 0° C. and 0.05 cm³ (0.75 mmole) of anhydrous ethylamine is added. Stirring is maintained for 2 hours while permitting the temperature to return to ambient temperature. The reaction mixture is then diluted with 20 cm³ of dichloroethane, washed initially with 0.1N HCl and then with water. The organic phase is dried on sodium sulfate and evaporated to dryness. The crude amide is recrystallized in hexane containing a trace of acetone. After drying, 210 mg of white crystals of N-ethyl-6-[(TTMDBF) carbonyl]-2-naphthalene carboxamide having the following characteristics: Melting point: 123°–125° C.; NMR ¹H 250 MHz conforming to the expected structure, are obtained.

Analysis of the product obtained gives the following results:

| Analysis | Calculated for $C_{30}H_{31}NO_3$ | Found |
| --- | --- | --- |
| C | 79.44 | 79.39 |
| H | 6.89 | 6.98 |
| N | 3.09 | 3.10 |
| O | 10.58 | 10.61 |

EXAMPLE 9

A gel is prepared by making the following formulation:

| | |
| --- | --- |
| Compound of Example 3(c) | 0.05 g |
| Erythromycin base | 4.000 g |
| Butylhydroxytoluene | 0.050 g |
| Hydroxypropyl cellulose, sold by Hercules under the trade name "KLUCEL HF" | 2.000 g |
| Ethanol (95%) sufficient amount for | 100.000 g |

This gel is applied to skin with dermatosis or to acne skin 1 to 3 times each day. A significant improvement is noted in about 6 to 12 weeks depending on the gravity of the disorder being treated.

EXAMPLE 10

The following formulation intended for packaging in a gelule is prepared:

| | |
| --- | --- |
| Compound of Example 3(c) | 0.06 g |
| Corn starch | 0.060 g |
| Lactose, sufficient amount for | 0.3000 g |

The gelules employed are made of gelatin, titanium oxide and a preservative. 1 to 3 gelules per day are administered to an adult individual in the treatment of psoriasis. A significant improvement is noted at the end of about 30 days.

EXAMPLE 11

An antiseborrhea lotion is prepared by admixing the following ingredients:

| | |
| --- | --- |
| Compound of Example 1 | 0.03 g |
| Propylene glycol | 5.00 g |
| Butylhydroxytoluene | 0.10 g |
| Ethanol (95%), sufficient amount for | 100.00 g |

This lotion is applied twice each day to the scalp exhibiting seborrhea. A significant improvement is noted in about 2 to 6 weeks.

EXAMPLES 12

A sunscreen cosmetic composition is prepared by admixing the following ingredients:

| | |
|---|---|
| Compound of Example 6 | 1 g |
| Benzylidene camphor | 4 g |
| Triglycerides of fatty acids | 31 g |
| Glycerol monostearate | 6 g |
| Stearic acid | 2 g |
| Cetyl alcohol | 1.2 g |
| Lanolin | 4.0 g |
| Preservatives | 0.3 g |
| Propanediol | 2.0 g |
| Trietnanolamine | 0.5 g |
| Perfume | 0.4 g |
| Demineralized water, sufficient amount for | 100.0 g |

EXAMPLE 13

A gel for topical application is prepared by admixing the following ingredients:

| | |
|---|---|
| Compound of Example 4 | 0.05 g |
| Ethanol | 43.00 g |
| α-tocopherol | 0.05 g |
| Carboxyvinyl polymer sold under the trade name "Carbopol 941" by Goodrich | 0.50 g |
| Triethanolamine, 20 weight percent aqueous solution | 3.80 g |
| Water | 9.30 g |
| Propylene glycol, sufficient amount for | 100.00 g |

In this Example, the compound of Example 4 can be replaced, in the same amounts, by that of Example 6.

This gel is applied to skin having dermatosis or to acne skin 1 to 3 times each day. A significant improvement is noted in a period from 6 to 12 weeks, depending on the gravity of the disorder being treated.

EXAMPLE 14

An anti-acne cream is prepared by admixing the following ingredients:

| | |
|---|---|
| Mixture of glycerol stearates and polyethylene glycol (75 moles) sold under the trade name "Gelot 64" by Gattefosse | 15 g |
| Stone oil, polyoxyethylenated with 6 moles of ethylene oxide, sold under the trade name "Labrafil M 2130 CS" b6 Gattefosse | 8 g |
| Perhydrosqualene | 10 g |
| Dye, sufficient amount | |
| Preservatives, sufficient amount | |
| Perfumes, sufficient amount | |
| Tioxolane | 0.4 g |
| Polyethylene glycol (molecular mass = 400) | 8 g |
| Purified water | 58.5 g |
| Disodium salt of ethylenediamine tetraacetic acid | 0.05 g |
| Compound of example 7 | 0.05 g |

This cream is applied to skin having dermatosis or to acne skin, 1 to 3 times each day. A significant improvement is noted in a period between 6 and 12 weeks depending on the gravity of the disorder being treated.

EXAMPLE 15

A hair lotion for combatting falling hair and for promoting hair growth is prepared by admixing the following ingredients:

| | |
|---|---|
| Propylene glycol | 20 g |
| Ethanol | 34.92 g |
| Polyethylene glycol (molecular mass = 400) | 40 g |
| Water | 4 g |
| Butylhydroxyanisole | 0.01 g |
| Butylhydroxytoluene | 0.02 g |
| Compound of Example 3(c) | 0.05 g |
| Compound sold under the trade name "Minoxidil" | 1 g |

This lotion is applied 2 times each day to the scalp exhibiting significant hair los. After 3 months of treatment, a significant improvement is observed.

In the formulation of this Example the compound of Example 3(c) can be replaced by that of Example 8.

EXAMPLE 16

A 0.5 g non-soluble tablet is prepared by admixing the following substances:

| | |
|---|---|
| Compound of Example 7 | 0.025 g |
| Lactose | 0.082 g |
| Stearic acid | 0.003 g |
| Purified talc | 0.015 g |
| Sweetening agent, sufficient amount | |
| Dye, sufficient amount | |
| Rice starch, sufficient amount for | 0.500 g |

1 to 3 tablets per day are administered orally to an adult individual suffering from psoriasis. A significant improvement is noted at the end of about 30 days.

EXAMPLE 17

A solution having 20 weight percent of active material is prepared by making the following formulation:

| | |
|---|---|
| Compound of Example 8 | 0.2 g |
| Polyethyleneglycol (molecular mass = 400) | 80.0 g |
| Ethanol, (95%) sufficient amount for | 100.0 g |

This solution is applied to acne skin 1 to 3 times per day and a significant improvement is noted after a period between 6 to 12 weeks, depending on the gravity of the disorder being treated.

EXAMPLE 18

An anti-seborrhea cream is prepared by making the following formulation:

| | |
|---|---|
| Polyoxyethylenated stearate (40 moles of ethylene oxide) sold under the trade name "Myrj 52" by Atlas | 4 g |
| Sorbitan monolaurate, polyoxyethylenated with 20 moles of ethylene oxide, sold under the trade name "Tween 20" by Atlas | 1.8 g |
| Mixture of glycerol mono and di-stearate, sold under the trade name "GELEOL" by Gattefosse | 4.2 g |
| Propyleneglycol | 10.0 g |

-continued

| | |
|---|---|
| Butylhydroxyanisole | 0.01 g |
| Butylhydroxytoluene | 0.02 g |
| Keto-stearyl alcohol | 6.2 g |
| Preservatives, sufficient amount | |
| Perhydrosqualene | 18.0 g |
| Mixture of caprylic - capric triglycerides, sold under the trade name "Miglyol 812" by Dynamit Nobel | 4 g |
| S-carboxymethyl cysteine | 3 g |
| Triethanolamine (99 wt percent) | 2.5 g |
| Compound of Example 5(c) | 0.02 g |
| Water, sufficient amount for | 100.00 g |

This cream is applied twice each day to skin having oily tendencies. A significant improvement is observed in a period between 2 and 6 weeks.

EXAMPLE 19

An anti-seborrhea cream is prepared by making the following formulation:

| | |
|---|---|
| Polyoxyethylene stearate (40 moles of ethylene oxide) sold under the trade name "Myrj 52" by Atlas | 4 g |
| Sorbitan monolaurate, polyoxyethylenated with 20 moles of ethylene oxide, sold under the trade name "Tween 20" by Atlas | 1.8 g |
| Mixture of glycerol mono and distearate, sold under the trade name "GELEOL" by Gattefosse | 4.2 g |
| Propyleneglycol | 10.0 g |
| Butylhydroxyanisole | 0.01 g |
| Butylhydroxytoluene | 0.02 g |
| Keto-stearyl alcohol | 6.2 g |
| Preservatives, sufficient amount | |
| Perhydrosqualene | 18 g |
| Mixture of caprylic-capric triglycerides, sold under the trade name "Miglyol 812" by Dynamit Nobel | 4 g |
| 5-amino-5-carboxy-3-thia pentanoate of 2-benzylthio ethylammonium | 3 g |
| Compound of Example 3(b) | 0.02 g |
| Water, sufficient amount for | 100 g |

This cream is applied twice each day to skin having oily tendencies. A significant improvement is noted in a period between 2 and 6 weks.

EXAMPLE 20

A lotion for the promotion of hair growth is prepared by admixing the following ingredients:

| | |
|---|---|
| Propylene glycol | 13.96 g |
| Polyethyleneglycol (molecular mass = 300) | 40 g |
| Polyethyleneglycol (molecular mass = 1500) | 32 g |
| Isopropanol | 12 g |
| Butylhydroxyanisole | 0.01 g |
| Butylhtdroxytoluene | 0.02 g |
| Compound of Example 5 | 0.05 g |
| Compound sold under the trade name "Minoxidil" | 2 g |

The lotion is applied to the scalp twice each day and, after 3 months of treatment, a significant improvement is noted.

EXAMPLE 21

An anti-acne kit comprises two parts:

| Part one | |
|---|---|
| (a) A gel is prepared by making the following formulation: | |
| Ethyl alcohol | 48.4 g |
| Propylene glycol | 50 g |
| Carboxyvinylpolymer, sold under the trade name "CARBOPOL 940" by Goodrich | 1 g |
| Diisopropanolamine (99 wt %) | 0.3 g |
| Butylhydroxyanisole | 0.05 g |
| Butylhydroxytoluene | 0.05 g |
| α-tocopherol | 0.1 g |
| Compound of Example 5 | 0.1 g |
| Part two | |
| (b) A gel is prepared by making the following formulation: | |
| Ethyl alcohol | 5 g |
| Propylene glycol | 5 g |
| Disodium salt of ethylene diamine tetraacetic acid | 0.05 g |
| Carboxyvinyl polymer sold under the trade name "CARBOPOL 940" by Goodrich | 1 g |
| Triethanolamine (99 wt %) | 1 g |
| Sodium lauryl sulfate | 0.1 g |
| Purified water | 75.05 g |
| Hydrated benzoyl peroxide at 25 wt % | 12.8 g |

The mixture of the two gels is made extemporaneously, weight for weight, at the moment of use. The resulting mixture is applied to skin with dermatosis or to acne skin 1 to 3 times each day. A significant improvement is noted in a period between 6 to 12 weeks according to the gravity of the disorder being treated.

What is claimed is:

1. A benzofuran compound having the formula (I)

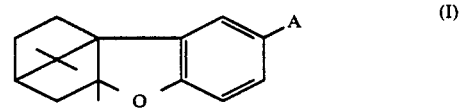

wherein
A is

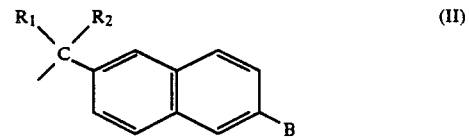

wherein
$R_1$ represents hydrogen, OH, $C_1$-$C_4$ alkoxy, $C_1$-$C_4$ acyloxy or $NH_2$;
$R_2$ represents hydrogen or $C_1$-$C_4$ alkoxy; or
$R_1$ and $R_2$ taken together form an oxo, methano or hydroxyimino radial; and
B represents
(a) $COOR_8$ wherein $R_8$ represents hydrogen or $C_1$-$C_{20}$ alkyl, or
(b) $COR_5$ wherein $R_5$ represents

wherein R$_6$ represents hydrogen and R$_7$ represents C$_1$–C$_6$ alkyl.

2. A benzofuran compound having the formula (I)

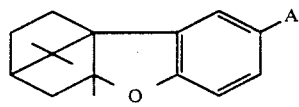  (I)

wherein
A is

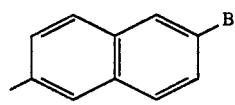  (III)

wherein
B is
(a) COR$_5$ wherein R$_5$ is

wherein R$_6$ represents hydrogen and R$_7$ represents C$_1$–C$_6$ alkyl, or
(b) COOR$_8$ wherein R$_8$ represents hydrogen or C$_1$–C$_{20}$ alkyl.

3. A benzofuran compound having the formula (I)

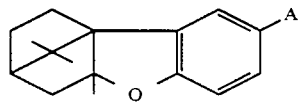  (I)

wherein
A is

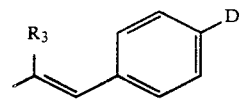  (V)

wherein
R$_3$ represents C$_1$–C$_6$ alkyl and
D represents —SCH$_3$.

4. A benzofuran compound having the formula (I)

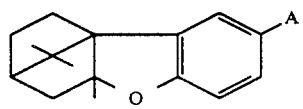  (I)

wherein A has the formula

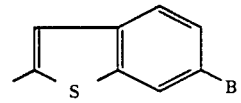  (IV)

wherein
B is COOR$_8$ wherein R$_8$ is hydrogen or C$_1$–C$_{20}$ alkyl.

* * * * *